United States Patent [19]

Schneider et al.

[11] Patent Number: 4,535,071

[45] Date of Patent: Aug. 13, 1985

[54] CATALYST FOR METHANOL SYNTHESIS AND METHOD OF PREPARING THE CATALYST

[75] Inventors: Michael Schneider, Ottobrunn-Riemerling; Karel Kochloefl, Moosburg; Jürgen Ladebeck, Landshut, all of Fed. Rep. of Germany

[73] Assignee: Süd Chemie Aktiengesellschaft, Munich, Fed. Rep. of Germany

[21] Appl. No.: 610,745

[22] Filed: May 16, 1984

[30] Foreign Application Priority Data

May 16, 1983 [DE] Fed. Rep. of Germany ....... 3317725

[51] Int. Cl.$^3$ .................... B01J 21/04; B01J 23/06; B01J 23/72
[52] U.S. Cl. ..................................... 502/342; 518/713
[58] Field of Search ........................................ 502/342

[56] References Cited

U.S. PATENT DOCUMENTS 3,790,505 2/1974 Casey et al. .................... 502/342
4,279,781 7/1981 Dienes et al. .................... 502/343

*Primary Examiner*—W. J. Shine
*Attorney, Agent, or Firm*—Wm. R. Price

[57] ABSTRACT

Catalyst for methanol synthesis, containing
(a) as catalytically active substances copper oxide and zinc oxide, which, if desired, may be at least partially reduced, and
(b) as thermostabilizing substance aluminum oxide.

The proportion of pores with a diameter of 20 to 75 Å (mesopores) is at least 20% and the proportion of pores with a diameter of more than 75 Å (macropores) is at most 80%. The desired pore distribution can be obtained by using colloidally dispersed aluminum oxide or hydroxide in the production of the catalyst.

28 Claims, No Drawings

CATALYST FOR METHANOL SYNTHESIS AND METHOD OF PREPARING THE CATALYST

FIELD OF THE INVENTION

The invention relates to a catalyst for methanol synthesis, containing
(a) as catalytically active substances copper oxide and zinc oxide, where, if desired, at least the copper oxide is reduced at least partially, and
(b) as thermostabilizing substance aluminum oxide.

BACKGROUND OF THE INVENTION

Such catalysts, which catalyze the transformation of CO, $CO_2$ and $H_2$ to methanol, have been known for some time. At temperatures of 200° to 300° C. and pressures between 30 and 250 bar they give satisfactory yields of methanol, and the length of their useful life is good. In these known catalysts, the atomic ratios between copper and zinc may vary, but generally the copper is present in excess. Furthermore, a part of the zinc component may be partially replaced by calcium, magnesium and/or manganese. The aluminum oxide used as thermostabilizing substance may also be partially replaced by chromium oxide.

DESCRIPTION OF THE PRIOR ART

Such catalysts are known, for example, from the German disclosure Nos. 1,956,007, 2,302,658 and 2,056,612 as well as from U.S. Pat. No. 4,279,781. In particular, U.S. Pat. No. 4,279,781 teaches that by the use of metal oxides difficult to reduce, such as aluminum oxide, the thermal resistance of the Cu/Zn system can be improved, definitely longer times on stream being obtained. The addition of thermostabilizing substances is, however, limited, since at too high a proportion of these substances, the selectivity and the activity of the Cu/Zn catalysts are impaired.

SUMMARY OF THE INVENTION

It is the object of the invention to provide catalysts of the initially defined kind which together with good activity and selectivity have a high thermal resistance or thermal stability. At a high thermal resistance, the useful life of the catalysts is longer, or respectively, they can be used at higher temperatures, at which the waste heat of the synthesis reaction can be better utilized economically. It has been found, surprisingly, that this problem can be solved in the initially defined catalysts by a certain pore structure, such that the proportion of pores with a diameter ranging from 20 to 75 Å (called mesopores in the following) is at least 20% and the proportion of pores with a diameter of more than 75 Å (called macropores in the following) is at most 80%. Preferably, the proportion of mesopores is in the range of 20 to 40, in particular in the range of 30 to 40%, and the proportion of macropores in the range of 80 to 60, in particular 70 to 60%. The proportion of pores with a pore diameter of less than 20 Å (micropores) is relatively small and is generally under 0.5%.

DESCRIPTION OF THE PREFERRED EMBODIMENT

Due to the pore distribution according to the invention it is possible to increase the proportion of the aluminum oxide used as thermal stabilizing substance without the conversion and selectivity of the methanol synthesis reaction being impaired. This is probably because under conditions close to the practice the synthesis reaction takes place inside the pores of the catalyst, the internal diffusion being an important factor and the active surface of the catalyst not being completely utilized. By activity tests on catalyst tablets of different size, it has been possible to establish that with decreasing size of the tablets, the degree of utilization and the yield of methanol increase, evidently because the diffusion of the reactants is favored and the surface reaction becomes rate-determining. At the same time, the quantity of formed organic by-products decreases, i.e. the selectivity improves, probably as a result of the shortened residence time of the reaction products or intermediate products in the mesopores of the catalyst.

It has further been established that an optimum yield of methanol is obtained when the atomic ratio Cu/Zn is between 2.8 and 3.8, preferably between 2.8 and 3.2, and when the proportion of $Al_2O_3$ is 8 to 12 wt. %, preferably 9 to 11 wt. %. Under these conditions, the attained degree of utilization of the catalysts of the invention (referred to as CO conversion) is 83 to 90%.

The catalysts of the invention further have preferably a specific surface of more than 80 $m^2/g$, preferably more than 100 $m^2/g$ (in the unreduced state).

The pore distribution according to the invention can be adjusted in a simple manner by modification of the aluminum oxide component. This fact is surprising inasmuch as generally the proportion of the aluminum oxide component is smaller than the proportion of the copper oxide-zinc oxide components.

The aluminum oxide component can be modified in the desired sense by using for the production of the catalyst colloidally dispersed aluminum oxide or hydroxide.

These colloidal modifications of the aluminum oxide component generally have primary particle sizes in the range of some 1,000 to 10,000 Å. They may be present in the form of xerogels, hydrogels or sols. Xerogels can be admixed as dry powders to the dry copper oxide-zinc oxide component or respectively to a precursor stage thereof, whereupon the resultant mixture is calcined.

However, the use of the aluminum oxide component in the form of hydrogels and sols is especially preferred. These can be added to the dry copper oxide-zinc oxide component or respectively precursor stages thereof.

Preferably, however, the catalysts of the invention can be obtained by precipitating the catalytically active copper oxide-zinc oxide component from aqueous solutions of the respective salts (e.g. the nitrates, sulfates, chlorides, acetates, etc.) with alkaline reacting substances in the presence of the aluminum oxide or hydroxide colloidally dispersed (as gel or sol). The mixture or precipitate obtained can be dried, calcined, tableted and, if desired, reduced. The reduction of the catalyst may alternatively be carried out at the beginning of the methanol synthesis reaction, as the synthesis gas contains hydrogen.

Preferably, one uses as alkaline reacting substances for the precipitation an alkali or ammonium carbonate or bicarbonate, preferably sodium carbonate or sodium bicarbonate. The use of potassium carbonate or potassium bicarbonate is less appropriate, because a residual content of potassium in the catalyst reduces the selectivity of the synthesis of methanol, and higher alcohols form. However, a residual content of sodium in the catalyst does not interfere, so that a precipitate produced with sodium carbonate or sodium bicarbonate need not be specially washed.

A further improvement of the pore structure in the direction of a higher proportion of mesopores can be achieved by carrying out the precipitation of the copper oxide-zinc oxide component in the presence of the colloidally divided aluminum oxide or hydroxide with the use of relatively dilute solutions of the alkaline reacting substances, at relatively low temperatures and at neutral or even weakly acid pH values.

The precipitation is carried out with a $NaHCO_3$ or $Na_2CO_3$ solution, preferably a solution having a concentration of 5 to 17 wt. % and preferably 8 to 12 wt. %. The precipitation temperature is appropriately 25° to 65° C., preferably 30° to 40° C. The addition of alkaline reacting substances is generally terminated when the pH value is in the range of 6.5 to 7.5, preferably 6.9 to 7.5.

For known catalysts, the precipitation is normally carried out at higher temperatures and higher solution concentrations of the alkaline reacting substances. Another preferred measure for improving the desired pore distribution involves drying the precipitate immediately after its production, i.e. preventing crystal maturation and aging of the precipitate in contact with the aqueous phase.

The invention is explained by the following examples:

COMPARISON EXAMPLE

For the precipitation of the catalyst precursor, two solutions are prepared:
Solution 1: 418 g copper nitrate and 50 g zinc oxide are dissolved in 1 liter water and 148 g of a 52.5% $HNO_3$ and subsequently mixed with a solution of 93.8 g $Al(NO_3)_3.9H_2O$ in 0.5 liter $H_2O$.
Solution 2: 410 g sodium carbonate are dissolved in 2 liters of water.

The solutions are heated separately to 68° C. and are combined under strong agitation in such a way that during the precipitation the pH value is 6.7. Under agitation at 68° C. the precipitate is aged in the mother liquor for another hour, then filtered and washed sodium-free with water. The filter cake is dried at 120° C. and thereafter calcined for 8 hours at 280° C.

The calcined product is comminuted and tabletted after addition of 2 wt. % graphite.

EXAMPLE 1

The procedure is analogous to that stated in the comparison example, but instead of the aluminum nitrate solution a colloidal aluminum metahydrate sol (AlO(OH) sol) (equivalent $Al_2O_3$ quantity) was used. This suspension was slowly mixed with 30 g of the 52.5% nitric acid with agitation at 50° C., to peptize the aluminum metahydrate particles. Then the sol was combined with the copper-zinc nitrate solution. The precipitation and further treatment of the catalyst precursor was identical to the procedure indicated in the comparison example.

EXAMPLE 2

The procedure of Example 1 is repeated except that the aluminum metahydrate suspension and the metal nitrate solution are combined at 40° C.

EXAMPLE 3

The procedure of Example 1 is repeated except that the precipitation is carried out at a pH value of 6.9.

EXAMPLE 4

For the precipitation of the catalyst precursor, two solutions are prepared:
Solution 1: 418 g copper nitrate and 50 g zinc oxide are dissolved in 1.6 liter water and 128 g 52.5% $HNO_3$ and thereafter mixed with the colloidal aluminum metahydrate gel.
Solution 2: 410 g sodium carbonate are dissolved in 3317 g water.

The precipitation and further treatment of the catalyst precursor was done identically to the procedure of the comparison example.

EXAMPLE 5

For the precipitation of the catalyst precursor, two solutions are prepared according to the procedure described in Example 4.

These are combined under strong agitation at 40° C. in such a way that during the precipitation the pH value is 6.9. After termination of the precipitation, at which the pH should not yet have exceeded the value 7.1, the precipitate is filtered and washed with water. The further treatment of the catalyst precursor is the same as that of the comparison example.

The chemical composition of the catalyst precursor is given in Table I.

TABLE I

| | Chemical composition of the catalyst precursor | | |
|---|---|---|---|
| Example No. | CuO (wt. %) | ZnO (wt. %) | $Al_2O_3$ (wt. %) |
| Comparison Example | 67.7 | 22.2 | 10.1 |
| Example 1 | 65.9 | 22.9 | 11.2 |
| Example 2 | 67.6 | 22.4 | 10.0 |
| Example 3 | 65.0 | 23.1 | 11.9 |
| Example 4 | 67.4 | 21.4 | 11.1 |
| Example 5 | 65.1 | 22.9 | 12.0 |

*Analysis of the calcined, graphite-free catalyst precursor

The physical properties of the catalyst precursor are given in Table II.

TABLE II

| Example | Spec. Surface ($m^2/g$) | Spec. Weight (g/liter) | Pore Volume (ml/g) | Pore Diameter 75-20 Å (%) | >75 Å (%) |
|---|---|---|---|---|---|
| Comparison ex. | 63 | 1280 | 0.24 | 18 | 82 |
| Ex. 1 | 113 | 1060 | 0.36 | 39 | 61 |
| Ex. 2 | 113 | 1040 | 0.42 | 34 | 66 |
| Ex. 3 | 107 | 1040 | 0.34 | 32 | 68 |
| Ex. 4 | 100 | 1070 | 0.34 | 42 | 58 |
| Ex. 5 | 127 | 1025 | 0.44 | 43 | 57 |

Remarks Concerning Table II:

The specific surface area was determined by the BET method. The pore volume and pore diameter were determined as follows:

The volume or pore size distribution for pores down to 75 Å was determined by means of mercury porosimetry. In a second measurement, using $N_2$ porosimetry (BET method), the pore volume and the distribution was determined for pores under 1000 Å. The proportion of the pore volume prorated to pores <75 Å was calculated and added to the volume determined by means of Hg porosimetry.

The activity of the catalysts of the invention in the methanol synthesis was tested as follows:

30 ml of catalyst precursor in the form of tablets were at first reduced in the reaction tube without pressure, the tablets being heated in streaming (50 liter/h) reduction gas (1.2% $H_2$, balance $N_2$) according to a temperature program to 235° C. From 235° C. to the synthesis temperature (250° C.) pure $H_2$ was used for flushing the reactor.

Then a synthesis gas of the following composition (in vol.-%) was passed over the catalyst compacts: $H_2$=75.3%, CO=10.8%, $CO_2$=3.9%; inert gases=10% ($CH_4$=7.2%, $N_2$=2.8%).

The reaction conditions were as follows:
Entrance temperature 250° C.
Pressure 50 bar
Gas space velocity (HSV)=10,000 vol. synthesis gas per vol. catalyst per hour.

The results of the activity measurement are given in Table III. With the catalysts of the invention, the methanol yield is higher than with the comparison catalyst. It should be noted further that as a result of the higher degree of conversion the methanol yield is especially elevated with those catalysts whose precursors were precipitated at temperatures below 60° C., at a slightly increased pH value, and from more dilute solutions than usual.

TABLE III

| Example | Space-Time Yield of Pure Methanol (kg/ltr · h) | Degree of Utilization $eta_{CO}$ (%) | Organic By-Products* (wt. %) |
| --- | --- | --- | --- |
| Comparison Example | 0.994 | 80.9 | 0.3 |
| Example 1 | 1.090 | 87.9 | 0.4 |
| Example 2 | 1.076 | 85.7 | 0.4 |
| Example 3 | 1.029 | 83.4 | 0.4 |
| Example 4 | 1.088 | 88.3 | 0.3 |
| Example 5 | 1.103 | 90.2 | 0.4 |

*The main portion consists of aliphatic ($C_2$-$C_5$) alcohols with a major part of $C_2H_5OH$.

We claim:

1. A catalyst, selective for the synthesis of methanol, which comprises:
   A. a major portion by weight of the oxides of copper and zinc;
   B. a minor portion by weight of aluminum oxide;
   C. in which the pore distribution of the finished catalyst is as follows:
      1. pores with a diameter in the range of 20–75 Å, constituting at least 20% and
      2. pores with a diameter greater than 75 Å, constituting no more than 80% of the catalyst.

2. A catalyst, as defined in claim 1, in which the proportion of pores with a diameter ranging from 20–75 Å, is in the range of from 20–40% and the proportion of pores with a diameter of more than 75 Å is in the range of from 60–80%.

3. A catalyst, as defined in claim 1, in which the atomic ratio of copper:zinc is in the range of 2.8:1 and 3.8:1.

4. A catalyst, as defined in claim 1, in which the atomic ratio of copper:zinc is in the range of from 2.8:1 and 3.2:1.

5. A catalyst, as defined in claim 1, in which the proportion of $Al_2O_3$ is from 8–12% by weight of the total of the catalyst.

6. A catalyst, as defined in claim 1, in which at least part of the copper oxide is at least partially reduced.

7. A catalyst, as defined in claim 1, which, in the unreduced state, has a specific surface of more than 80 $m^2/g$.

8. A catalyst, as defined in claim 1, which, in the unreduced state, has a specific surface of more than 100 $m^2/g$.

9. A catalyst, as defined in claim 1, in which the aluminum oxide of the finished catalyst has been derived from a colloidally dispersed aluminum oxide or colloidally dispersed aluminum hydroxide.

10. A catalyst, as defined in claim 1, which has been prepared by the co-precipitation of the copper and zinc constituents from an aqueous solution of soluble salts of said constituents, by the addition of an alkaline reacting substance in the presence of colloidally dispersed aluminum oxide or hydroxide.

11. A catalyst, as defined in claim 10, in which the precipitation has been carried out with an alkali or ammonium carbonate or bicarbonate.

12. A catalyst, as defined in claim 10, in which the precipitation is carried out with a sodium carbonate or bicarbonate solution, at a concentration of from about 5–17% by weight.

13. A catalyst, as defined in claim 10, in which the precipitation is carried out with a sodium bicarbonate or carbonate solution in a concentration of between 8–12% by weight.

14. A catalyst, as defined in claim 10, in which the precipitation is carried out at a temperature of between 25°–65° C.

15. A catalyst, as defined in claim 10, in which the precipitation has been carried out at a temperature of between 30°–40° C.

16. A catalyst, as defined in claim 10, in which the precipitation is carried out at a pH value in the range of from 6.5–7.5.

17. A catalyst, as defined in claim 10, in which the precipitation is carried out at a pH value in the range of from 6.9–7.5.

18. A catalyst, as defined in claim 10, in which the precipitate is separated from the mother liquor, immediately after precipitation, and washed and dried.

19. A method of making a methanol synthesis catalyst, which comprises the steps of:
   A. forming an aqueous solution of the water-soluble salts of copper and zinc;
   B. forming an aqueous solution of an alkaline-reacting substance;
   C. forming an aqueous solution of a colloidally dispersed aluminum oxide or hydroxide;
   D. mixing said aqueous solution of alkaline-reacting substances with said aqueous solution of copper and zinc and precipitating the insoluble components of copper and zinc;
   E. admixing said precipitate with said colloidal suspension of aluminum oxide or hydroxide;
   F. separating said mixture from said mother liquor and drying said precipitate;
   G. calcining said precipitate at a temperature sufficient to convert the insoluble salts of copper and zinc over to the oxide.

20. A method of preparing a catalyst, as defined in claim 19, in which the copper oxide-zinc oxide component is precipitated in the presence of the colloidally dispersed aluminum oxide or hydroxide.

21. The method of preparing a catalyst, as defined in claim 19, in which the precipitation is carried out with an alkali or ammonium carbonate or bicarbonate.

22. A method of preparing a catalyst, as defined in claim 19, in which the precipitation is carried out with sodium carbonate or bicarbonate in a weight concentration of from 5–17%.

23. A method of preparing a catalyst, as defined in claim 19, in which the precipitation is carried out with a sodium carbonate or bicarbonate with a weight concentration of from 8–12%.

24. A method of preparing catalysts, as defined in claim 19, in which the precipitation is carried out at a temperature of 25°–65° C.

25. A method of preparing catalysts, as defined in claim 19, in which the precipitation is carried out at a temperature in the range of from 30°–40° C.

26. A method of preparing catalysts, as defined in claim 19, in which the precipitation is carried out at a pH value in the range of from 6.5–7.5.

27. A method of preparing catalysts, as defined in claim 19, in which the precipitation is carried out at a pH value in the range of from 6.9–7.5.

28. A method of preparing catalysts, as defined in claim 19, in which the precipitate is immediately separated from the mother liquor, washed and dried.

* * * * *